United States Patent
Park et al.

(10) Patent No.: US 9,782,606 B2
(45) Date of Patent: Oct. 10, 2017

(54) INTEGRATED TARGET STRUCTURE FOR GENERATING CHARGED PARTICLE AND DRIVING METHOD OF MEDICAL APPLIANCE USING THE SAME

(71) Applicant: ELECTRONICS AND TELECOMMUNICATIONS RESEARCH INSTITUTE, Daejeon (KR)

(72) Inventors: Hyung Ju Park, Suwon (KR); Moon Youn Jung, Daejeon (KR); Won Bae Cho, Daejeon (KR); Ji Su Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/082,685

(22) Filed: Mar. 28, 2016

(65) Prior Publication Data

US 2016/0287899 A1 Oct. 6, 2016

(30) Foreign Application Priority Data

Mar. 30, 2015 (KR) ........................ 10-2015-0044497

(51) Int. Cl.
*G21K 5/04* (2006.01)
*A61N 5/10* (2006.01)
*H05H 6/00* (2006.01)

(52) U.S. Cl.
CPC ............. *A61N 5/10* (2013.01); *A61N 5/1075* (2013.01); *H05H 6/00* (2013.01); *A61N 5/1049* (2013.01); *A61N 2005/1072* (2013.01); *A61N 2005/1074* (2013.01); *A61N 2005/1088* (2013.01); *G21K 5/04* (2013.01); *H05H 2245/122* (2013.01)

(58) Field of Classification Search
CPC .............. A61N 5/10; A61N 2005/1088; A61N 2005/1074; A61N 2005/1072; A61N 5/1075; G21K 5/00; G21K 5/04; H05H 5/00; H05H 2245/122
USPC ........... 250/423 R, 424, 423 P, 492.1, 492.2, 250/492.21, 492.22, 492.23, 492.3; 600/1
See application file for complete search history.

(56) References Cited

U.S. PATENT DOCUMENTS

| 8,217,366 | B2 | 7/2012 | Jung et al. | |
| 9,033,964 | B2 | 5/2015 | Cho et al. | |
| 2012/0280138 | A1* | 11/2012 | Choi | C23C 14/0005 250/423 P |

(Continued)

FOREIGN PATENT DOCUMENTS

| KR | 10-1295702 B1 | 8/2013 |
| KR | 10-2013-0123059 A | 11/2013 |

(Continued)

*Primary Examiner* — Nicole Ippolito (57) ABSTRACT

Provided herein is an integrated target structure for generating charged particles. The integrated target structure according to an embodiment of the present disclosure includes a target layer emitting charged particles depending on an irradiation of a laser beam, an optical component controlling at least one of the laser beam and the charged particles, and a support body supporting the target layer and the optical component using one structure.

16 Claims, 5 Drawing Sheets

(56) References Cited

U.S. PATENT DOCUMENTS

2013/0158632 A1 6/2013 Park et al.
2013/0172865 A1 7/2013 Cho et al.

FOREIGN PATENT DOCUMENTS

| KR | 10-2014-0067433 A | 6/2014 |
| KR | 10-1430635 B1 | 8/2014 |

* cited by examiner

INTEGRATED TARGET STRUCTURE FOR GENERATING CHARGED PARTICLE AND DRIVING METHOD OF MEDICAL APPLIANCE USING THE SAME

CROSS-REFERENCE TO RELATED APPLICATION

The present application claims priority to Korean patent application number 10-2015-0044497 filed on Mar. 30, 2015, the entire disclosure of which is incorporated herein in its entirety by reference.

BACKGROUND

Field of Invention

Various embodiments of the present disclosure relate to a medical appliance, and more particularly, to an integrated target structure for generating charged particles and a driving method of a medical appliance using the same.

Description of Related Art

Generally, modern people living in a complicated society have been difficult to maintain good health due to a lot of stress, irregular meals, etc. In particular, modern people are highly likely to die of a malignant tumor, that is, a cancer or a tumor. The incidence of cancer tends to be increased in society and therefore national measures have been urgently required. Therefore, cancer treatments are becoming the center of attention.

As the cancer treatments, there are various treatments such as radiotherapy, a surgical operation, chemotherapy, magnetic field treatment, and thermotherapy.

In particular, the cancer treatment using radiation has been the most widely used along with the surgical operation and the chemotherapy. As the cancer treatment using radiation, there are various treatments such as X-ray therapy, electron beam therapy, and charged particle treatment (or proton beam therapy).

The X-ray therapy is the cheapest treatment that may be implemented using a simple apparatus and has been the most commonly used among the cancer treatments using radiation. Further, the electron beam therapy has been settled in earnest as one of the cancer treatments using radiation by realizing the miniaturization of an electron accelerator in 1980's. However, the X-ray treatment and the electron beam treatment breaks hydrogen bonds in cancer cells to destruct DNAs of the cancer cells and involves a side effect of damaging healthy cells present on a traveling path of beam. Therefore, as a method for decreasing a radiation exposure to normal cells, technologies of intensity-modulated radiation therapy (IMRT), tomography, a cyber knife, etc., have been developed, but do not completely resolve the foregoing side effect.

The charged particle treatment may selectively and locally treat a cancer and therefore has been in limelight as patent-friendly treatment.

An ion beam therapeutic apparatus needs a sufficient space (more than three-story building) for an accelerator (cyclotron or synchrotron), a gantry, radiation shielding facilities, etc., and a lot of installation cost. Further, a lot of manpower and cost are required to maintain the ion beam therapeutic apparatus.

The laser beam therapeutic apparatus for the charged particle treatment needs a narrower installation space (for example, 1/10) and lower maintenance cost than the foregoing ion beam therapeutic apparatus. However, the existing laser beam therapeutic apparatus needs to separately install targets and optical components for generating charged particles and therefore is difficult to cope with patient characteristics.

SUMMARY

Various embodiments of the present disclosure are directed to an integrated target structure for generating charged particles in which a target, an optical component, etc., are integrally formed and a driving method of a medical appliance using the same.

One embodiment of the present disclosure provides an integrated target structure, including: a target layer configured to emit charged particles depending on an irradiation of laser beam; an optical component configured to control at least one of the laser beam and the charged particles; and a support body configured to support the target layer and the optical component using one structure.

The optical component may include at least one of: a collimator configured to collimate the laser beam; a first filter configured to control characteristics of the laser beam; an amplifier configured to amplify the laser beam; and a second filter configured to penetrate only charged particles having specific energy among the charged particles.

Another embodiment of the present disclosure provides a medical appliance, including: an integrated target structure; a light source configured to irradiate a laser beam to the integrated target structure; and a 3D printer configured to manufacture the integrated target structure.

The medical appliance may further include: a scanner configured to scan the integrated target structure manufactured by the 3D printer; and a sensor configured to measure characteristics of charged particles emitted from the integrated target structure.

The integrated target structure may include: a target layer configured to emit charged particles depending on an irradiation of laser beam; an optical component configured to control at least one of the laser beam and the charged particles; and a support body configured to support the target layer and the optical component using one structure.

The optical component may include at least one of: a collimator configured to collimate the laser beam; a first filter configured to control characteristics of the laser beam; an amplifier configured to amplify the laser beam; and a second filter configured to penetrate only charged particles having specific energy among the charged particles.

Still another embodiment of the present disclosure provides a driving method of a medical appliance, including: tracking a position of a patient's tumor; measuring characteristics of a laser beam generated from a light source; simulating an integrated target structure for generating charged particles depending on the position of the tumor and the characteristics of the laser beam; and manufacturing the integrated target structure using a 3D printer based on the simulated result.

The driving method may further include: scanning the integrated target structure manufactured by the 3D printer using a scanner; and controlling the 3D printer depending on the scanned result.

The driving method may further include: irradiating the charged particles emitted from the integrated target structure to the tumor; and measuring characteristics of the charged particles emitted from the integrated target structure.

The present disclosure provides the integrated target structure for generating charged particles and the driving method of a medical appliance using the same, in which the target layer for generating charged particles and the optical components may be integrally formed. If the target layer and the optical components are integrally formed, the structure of the integrated target structure may be easily changed depending on the patient's characteristics, and thus the desired charged particles of energy may be generated. Further, when the target structure is integrated, the target structure may be manufactured using the 3D printer.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

DETAILED DESCRIPTION

Hereinafter, embodiments will be described in greater detail with reference to the accompanying drawings. Embodiments are described herein with reference to cross-sectional illustrations that are schematic illustrations of embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but may include deviations in shapes that result, for example, from manufacturing. In the drawings, lengths and sizes of layers and regions may be exaggerated for clarity. Like reference numerals in the drawings denote like elements.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present disclosure. Furthermore, 'and/or' may include any one of or a combination of the components mentioned.

Furthermore, a singular form may include a plural from as long as it is not specifically mentioned in a sentence. Furthermore, "include/comprise" or "including/comprising" used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

It is also noted that in this specification, "connected/coupled" refers to one component not only directly coupling another component but also indirectly coupling another component through an intermediate component. On the other hand, "directly connected/directly coupled" refers to one component directly coupling another component without an intermediate component.

Figure 1:
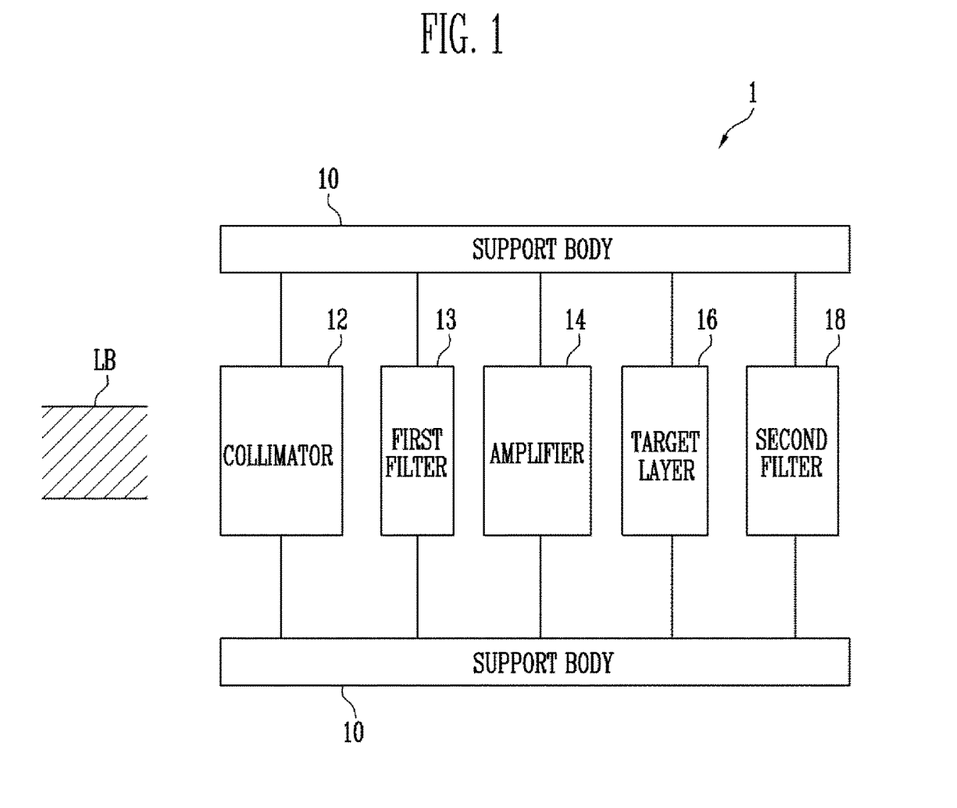
FIG. 1 is a diagram conceptually illustrating an integrated target structure according to an embodiment of the present disclosure.

FIG. 1 is a diagram conceptually illustrating an integrated target structure according to an embodiment of the present disclosure.

Referring to FIG. 1, an integrated target structure 1 according to an embodiment of the present disclosure includes a collimator 12, a first filter 13, an amplifier 14, a target layer 16, a second filter 18, and a support body 10. In this configuration, the collimator 12, the first filter 13, the amplifier 14, and the second filter 18 are used as optical components controlling a laser beam and charged particles.

The support body 10 supports the collimator 12, the first filter 13, the amplifier 14, the target layer 16, and the second filter 18 using one structure. The target structure including the collimator 12, the first filter 13, the amplifier 14, the target layer 16, and the second filter 18 may be integrally formed by the support body 10. The support body 10 may have various shapes corresponding to the structure of the collimator 12, the first filter 13, the amplifier 14, the target layer 16, and the second filter 18.

The collimator 12 may collimate a laser beam LB supplied from an external light source and change a path of the laser beam LB depending on the structure. For example, the collimator 12 has a funnel shape and focuses the laser beam LB from a light source on the amplifier 14. The collimator 12 may be made of metal, etc.

The laser beam LB is generated from the light source and may be set to have a wavelength of about 800 nm to 1000 nm and a frequency of about 1 to 3 THz.

The laser beam LB may include any one of a nanosecond laser, a picosecond laser, a femtosecond laser, a helium-neon laser, an argon laser, a helium-cadmium laser, a carbon dioxide laser, a carbonic acid gas laser, a ruby laser, a glass laser, a yttrium aluminum garnet (YAG) laser, a yttrium lithium fluoride (YLF) laser, a dye laser, a hetero junction laser, a quantum well laser, and a quantum dot laser.

Meanwhile, the laser beam LB is not limited to the kind of laser as described above, and any laser may be used as long laser it may generate a high-energy laser beam.

The first filter 13 is an optical filter and controls optical characteristics of the laser beam LB supplied from the collimator 12. For example, when the laser beam LB is a pulse laser, the first filter 13 may control pulse characteristics of the laser beam LB so that the laser beam LB has high energy.

The amplifier 14 may amplify the laser beam LB supplied from the first filter 13 and supply the amplified laser beam LB to the target layer 16. For this purpose, the amplifier 14 may be patterned in a predetermined shape and then may be formed on the target layer 16. Here, the amplifier 14 may be various patterning shapes as long as it may amplify the laser beam LB.

The target layer 16 generates charged particles corresponding to the laser beam LB incident from the amplifier 14. The target layer 16 may be made of at least one of metal materials and compounds thereof. For example, the target layer 16 may include at least one of inert metal materials such as platinum, gold, and silver. The target layer 16 is supported by the support body 10 and therefore may be formed regardless of a thickness. For example, even though the target layer 16 is formed thinly, the damage of the target layer due to the support by the support body 10 may be prevented.

Figure 2:
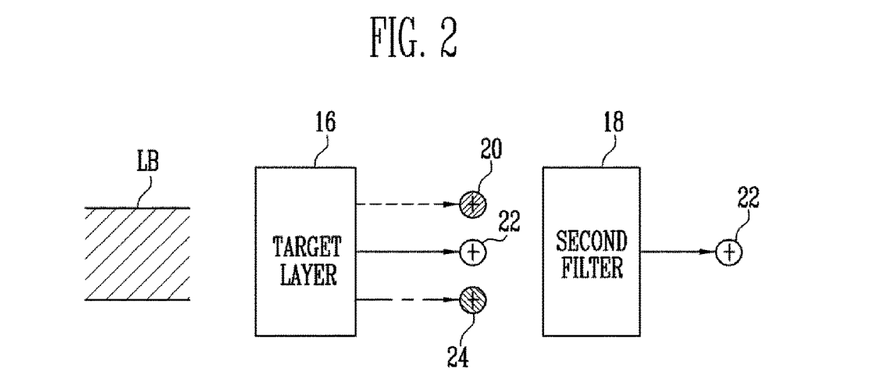
FIG. 2 is a diagram conceptually illustrating a role of a target layer and a filter illustrated in FIG. 1.

As illustrated in FIG. 2, the charged particles (for example, protons 20, 22, and 24) having different energies are generated from the target layer 16. In this case, the energy of the charged particles 20, 22, and 24 may be variously set due to the energy of the laser beam LB and the structure of the target layer 16. For example, the energy of the charged particles 20, 22, and 24 may be set to be 70 MeV to 250 MeV. Here, the charged particles having approximately 70 MeV may be used to treat an ocular cancer. Further, the charged particles having 250 MeV energy may be used to treat cancers located at the recesses of a human body. For example, the charged particles having 250 MeV energy may penetrate up to 20 cm of a human body.

The first charged particles 20 generated from the target layer 16 may have relatively higher energy and the second charged particles 22 may have relatively medium energy. Further, the third charged particles 24 generated from the target layer 16 may have relatively lower energy.

Here, the first to third charged particles 20 to 24 have different penetration depths of a human body depending on energy. For example, the first charged particles 20 having the high energy are penetrated as much as a first depth of a human body, the second charged particles 22 having the medium energy are penetrated as much as a second depth shallower than the first depth, and the third charged particles 24 having the low energy are penetrated as much as a third depth shallower than the second depth.

The second filter 18 penetrates charged particles having specific energy among the charged particles 20, 22, and 24 generated from the target layer 16 and interrupts charged particles having the rest energy other than the specific energy. For example, as illustrated in FIG. 2, the second filter 18 may penetrate the second charged particle 22 and cut off the first charged particle 20 and the third charged particle 24 depending on a patient's tumor. The charged particles 22 penetrating through the second filter 18 are supplied in a charged particle beam form.

Meanwhile, the present disclosure already describes that the integrated target structure 1 includes the collimator 12, the first filter 13, the amplifier 14, the target layer 16, and the second filter 18 but is not limited thereto. For example, the integrated target structure essentially includes the target layer 16 and may selectively include the collimator 12, the first filter 13, the amplifier 14, and the second filter 18. For example, the integrated target structure 1 may be changed to various forms depending on a patient's tumor.

In addition, the target structure 1 according to the embodiment of the present disclosure has the integrated structure, and therefore may be manufactured by a 3D printer. When the integrated target structure 1 is formed by the 3D printer, the structure of the integrated target structure 1 may be easily changed depending on a patient's tumor.

Figure 3:
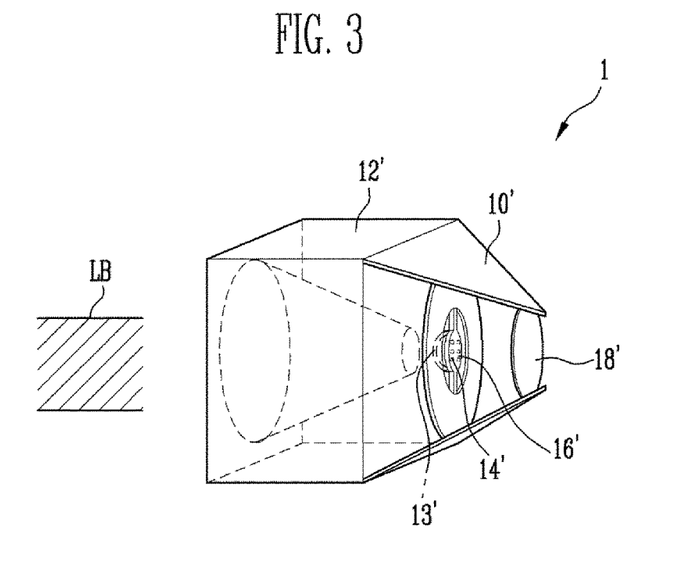
FIG. 3 is a diagram illustrating a first embodiment of the integrated target structure that may be implemented corresponding to the conceptual diagram of FIG. 1.

FIG. 3 is a diagram illustrating a first embodiment of the integrated target structure that may be implemented corresponding to the conceptual diagram of FIG. 1.

Referring to FIG. 3, the integrated target structure 1 according to a first embodiment of the present disclosure includes a support body 10', a collimator 12', a first filter 13', an amplifier 14', a target layer 16', and a second filter 18'.

The collimator 12' focuses the laser beam LB on the amplifier 14' and the target layer 16'. For this purpose, the collimator 12' may be formed in a funnel shape and may control the traveling path of the laser beam LB using an angle of the funnel.

The first filter 13' controls optical characteristics of the laser beam LB supplied from the collimator 13'.

The amplifier 14' is formed in a micro nano structure to have single energy simultaneously with amplifying the laser beam LB. The amplifier 14' is positioned between the collimator 12' and the target layer 16'. For example, the amplifier 14' may be formed on, for example, the target layer 16' (in FIG. 3, the amplifier 14' is not actually observed and therefore is shown by a dotted line).

The target layer 16' generates charged particles corresponding to a laser beam LB incident from the amplifier 14'. Here, the target layer 16' has a shape and a thickness to generate the desired charged particles depending on a patient's tumor.

The second filter 18' penetrates only the charged particles having the specific energy among the charged particles generated from the target layer 16'. The charged particles penetrating through the second filter 18' may be controlled depending on a size, a depth, etc., of the patient's tumor.

The support body 10' supports the collimator 12', the first filter 13', the amplifier 14', the target layer 16', and the second filter 18' using one structure. The collimator 12', the first filter 13', the amplifier 14', the target layer 16', and the second filter 18' may be integrally formed by the support body 10.

Meanwhile, the support body 10', the collimator 12', the first filter 13', the amplifier 14', the target layer 16', and the second filter 18' that are described above may be integrally formed by the 3D printer.

Figure 4:
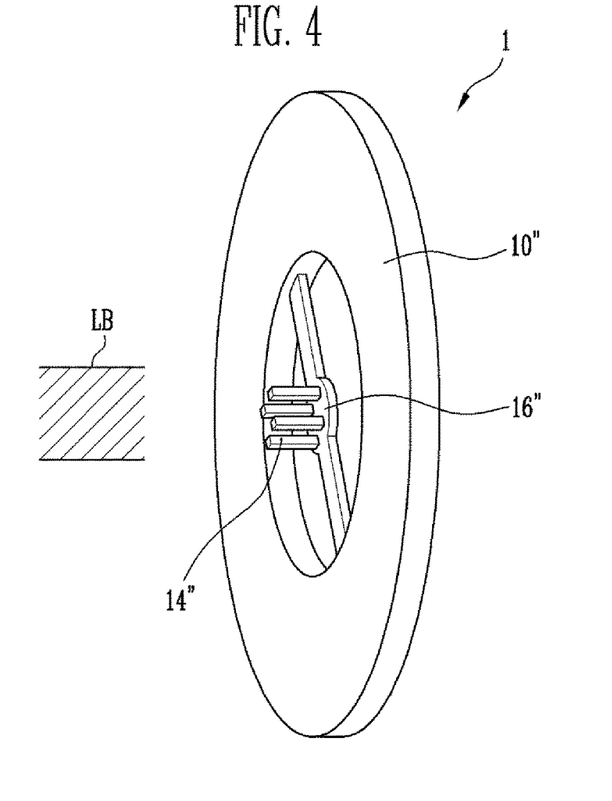
FIG. 4 is a diagram illustrating a second embodiment of the integrated target structure that may be implemented corresponding to the conceptual diagram of FIG. 1.

FIG. 4 is a diagram illustrating a second embodiment of the integrated target structure that may be implemented corresponding to the conceptual diagram of FIG. 1.

Referring to FIG. 4, the integrated target structure 1 according to a second embodiment of the present disclosure includes a support body 10", an amplifier 14", and a target layer 16".

The amplifier 14" is formed in a micro nano structure to have single energy simultaneously with amplifying the laser beam LB supplied from the light source.

The target layer 16" generates charged particles corresponding to a laser beam LB incident from the amplifier 14". Here, the target layer 16" has a shape and a thickness to generate the desired charged particles depending on a patient's tumor.

The support body 10" has a circular shape and supports the amplifier 14" and the target layer 16" using one structure.

The amplifier 14" and the target layer 16" may be integrally formed by the support body 10".

The support body 10", the amplifier 14", and the target layer 16" that are described above may be integrally formed by the 3D printer. When the integrated target structure 1 is manufactured by the 3D printer, the amplifier 14" having the micro nano structure, etc., may be easily and simply manufactured.

Meanwhile, according to the second embodiment of the present disclosure, the collimator 12, the first filter 13, and the second filter 18 included in the conceptual diagram of FIG. 1 are removed. That is, the configuration of the integrated target structure 1 according to the embodiment of the present disclosure may be variously controlled.

Figure 5:
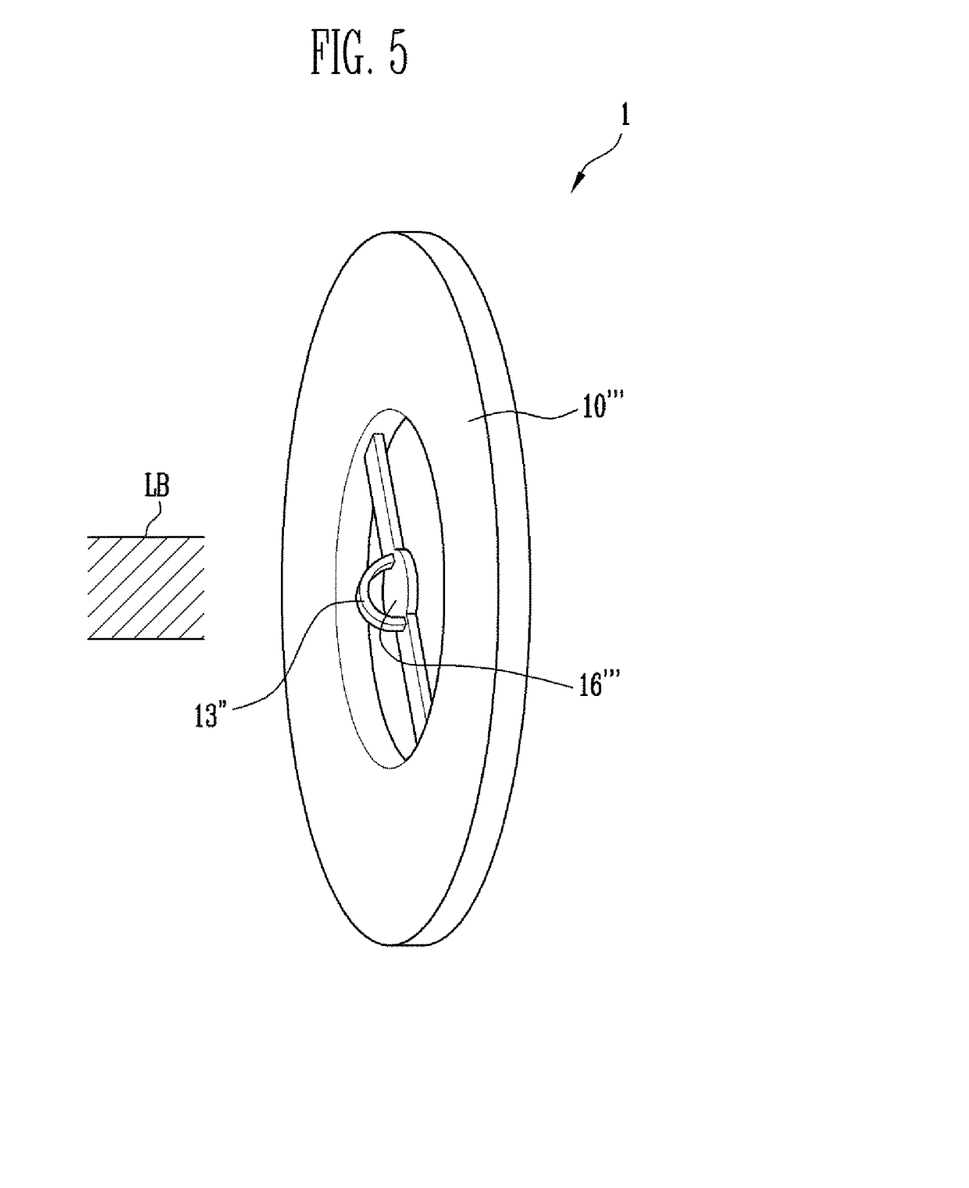
FIG. 5 is a diagram illustrating a third embodiment of the integrated target structure that may be implemented corresponding to the conceptual diagram of FIG. 1.

FIG. 5 is a diagram illustrating a third embodiment of the integrated target structure that may be implemented corresponding to the conceptual diagram of FIG. 1.

Referring to FIG. 5, the integrated target structure 1 according to a third embodiment of the present disclosure includes a support body 10''', a first filter 13'', and a target layer 16'''.

The first filter 13'' controls characteristics of the laser beam LB.

The target layer 16''' generates charged particles corresponding to a laser beam LB incident from the light source. Here, the target layer 16''' has a shape and a thickness to generate the desired charged particles depending on a patient's tumor.

The support body 10''' has a circular shape and supports a first filter 13'' and the target layer 16''' using one structure. The first filter 13'' and the target layer 16''' may be integrally formed by the support body 10'''.

The support body 10''', the first amplifier 13'', and the target layer 16''' that are described above may be integrally formed by the 3D printer. When the integrated target structure 1 is manufactured by the 3D printer, a hemispherical amplifier 18'', etc., may be easily and simply manufactured.

Figure 6:
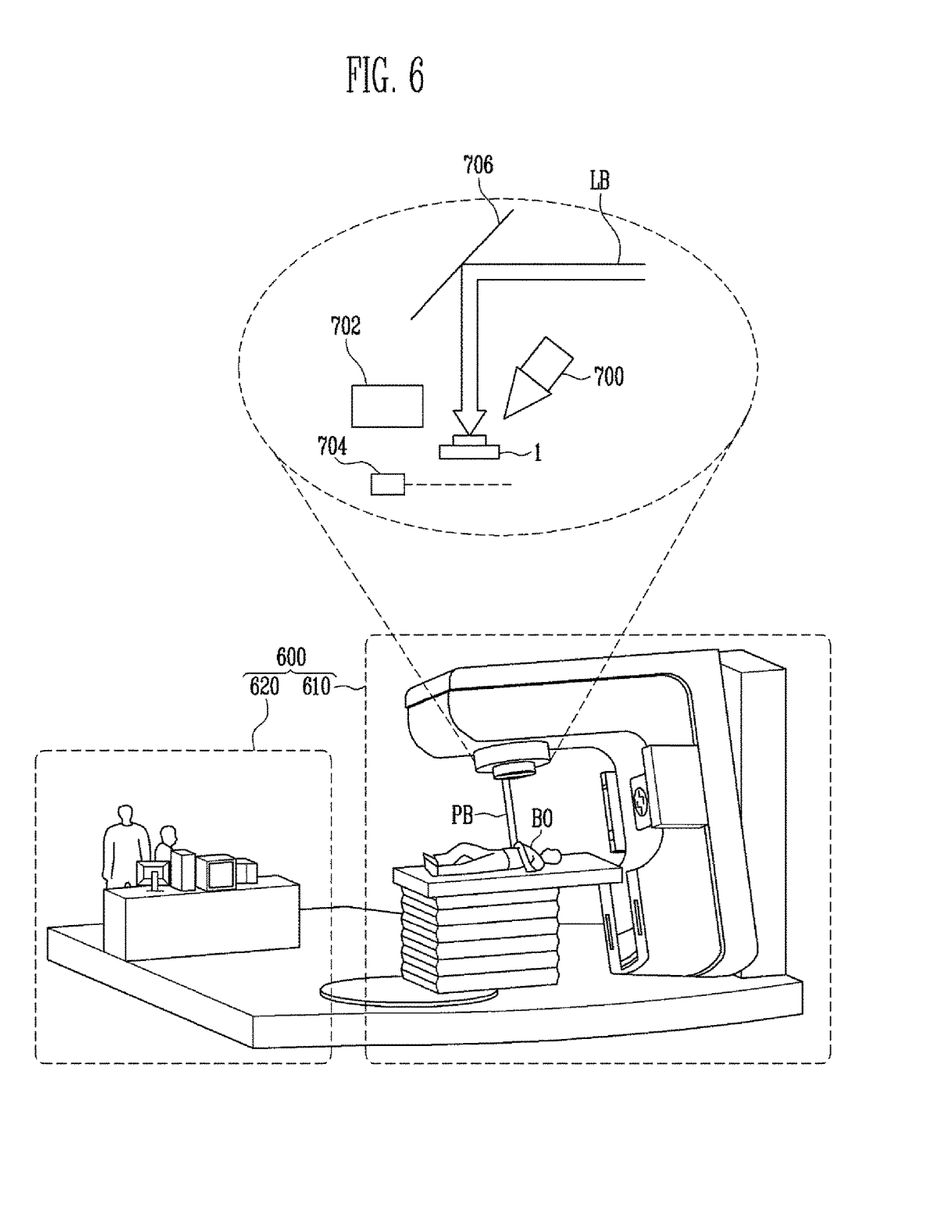
FIG. 6 is a diagram illustrating an embodiment of a medical appliance according to an embodiment of the present disclosure.

FIG. 6 is a diagram illustrating an embodiment of a medical appliance according to an embodiment of the present disclosure.

Referring to FIG. 6, a mechanical appliance 600 according to an embodiment of the present disclosure includes a charged particle beam generator 610 and a controller 620.

Figure 7:
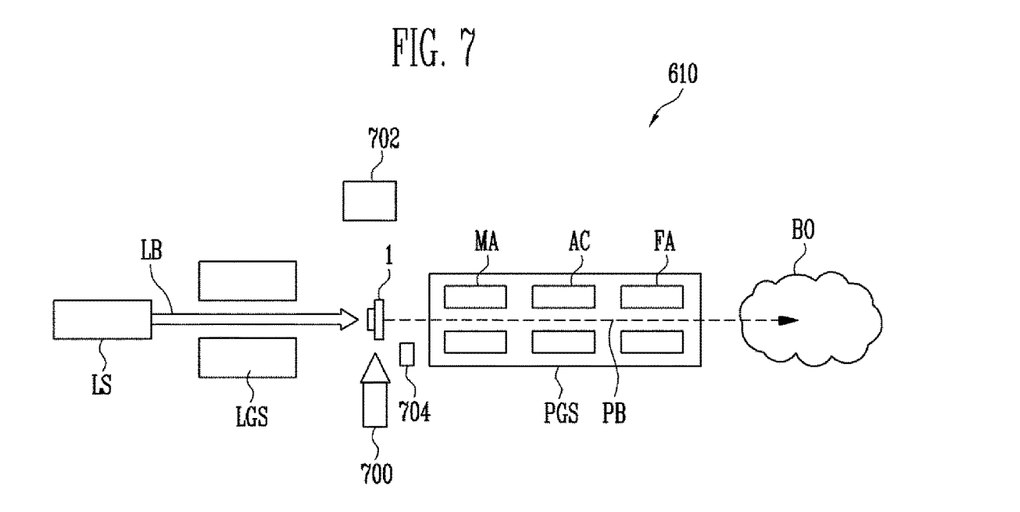
FIG. 7 is a diagram illustrating an embodiment of an apparatus for generating a charged particle beam of FIG. 6.

As illustrated in FIG. 7, the charged particle beam generator 610 includes a light source LS for generating the laser beam LB and the integrated target structure 1. In this configuration, the integrated target structure 1 may be one of those according to the embodiments with reference to FIG. 5.

In addition, the charged particle beam generator 610 may include a light guide structure (LGS) guiding the laser beam LB and a charged particle beam guide structure (PGS) guiding a charged particle beam PB (that is, charged particles) emitted from the integrated target structure 1 to a biological object BO (for example, patient's tumor).

The light guide structure LGS may be positioned between the light source LS and the integrated target structure 1 and may include a reflector 706, etc.

The charged particle beam guide structure PGS is interposed between the integrated target structure 1 and the biological object BO and may include at least one of a mass spectrometer MA, an accelerator AC, and a focusing apparatus FA.

In addition, the charged particle beam generator 610 according to the embodiment of the present disclosure may further include a 3D printer 700, a scanner 702, and a sensor 704.

The 3D printer 700 is controlled by the controller 620 to manufacture the integrated target structure 1.

The scanner 702 scans the shape of the integrated target structure 1 manufactured by the 3D printer 700 and supplies the scanned shape to the controller 620.

The sensor 704 measures the characteristics of the charged particle beam PB emitted from the integrated target structure 1 and supplies the measured characteristics to the controller 620.

The controller 620 controls the charged particle beam generator 610 simultaneously with providing a user interface. In particular, the controller 620 may use the 3D printer 700, the scanner 702, and the sensor 704 to design the integrated target structure 1.

Figure 8:
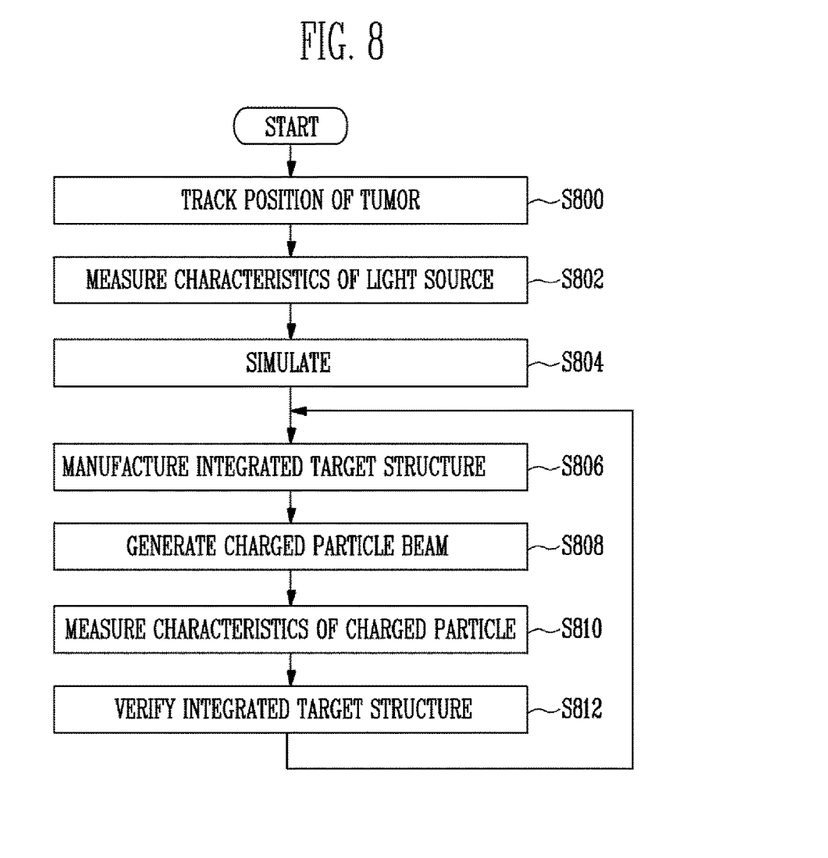
FIG. 8 is a diagram illustrating an embodiment of a driving method of a medical appliance according to an embodiment of the present disclosure.

FIG. 8 is a diagram illustrating an embodiment of a driving method of a medical appliance according to an embodiment of the present disclosure.

<Understand Patient Characteristics (S800)>

First, the medical appliance 600 tracks a position of the patient's tumor. For example, the medical appliance 600 may perform a predetermined test to understand a width, a depth, etc., of the tumor. The tumor understood in the step S800 is determined as the biological object BO to be treated by the charged particle beam PB. In addition, in the step S800, the patient's characteristics may also be input to the controller 620 from the outside.

<Measure Characteristics of Light Source (S802)>

After the patient's characteristics are understood, the medical appliance 600 measures the characteristics of the light source LS. The laser beam LB generated from the light source LS is set as various outputs and in the step S802, the output of the laser beam LB is understood. In addition, in the step S802, the characteristics of the light source LS may also be input to the controller 620 from the outside.

<Simulate (S804)>

In the step S804, the medical appliance 600 designs the integrated target structure 1 depending on the characteristics of the biological object BO and the characteristics of the light source that are understood in the steps S800 and S802. Here, the integrated target structure 1 may automatically design the integrated target structure 1 meeting the characteristics of the biological object BO and the characteristics of the light source based on various simulations.

<Manufacture Integrated Target Structure (S806)>

After the integrated target structure 1 is designed, the 3D printer 700 manufactures the integrated target structure 1 corresponding to the design in the step S804. By the 3D printer 700, the integrated target structure 1 may be easily and quickly manufactured even though the structure is complicated. In addition, the scanner 702 scans the shape of the integrated target structure 1 manufactured by the 3D printer 700 and supplies the scanned shape to the controller 620. The controller 620 controls the 3D printer 700 corresponding to the scanned result so that integrated target structure 1 may be manufactured in the desired shape.

<Generate Charged Particle Beam (S808)>

In the step S806, after the integrated target structure 1 is generated, the medical appliance 600 irradiates the charged particle beam PB to the biological object BO. That is, in the step S808, the medical appliance 600 uses the integrated target structure 1 to treat a patient's tumor.

<Measure Characteristics of Charged Particle Beam (S810)>

When the charged particle beam PB is irradiated to the biological object BO, the sensor 704 measures the characteristics of the charged particle beam and transmits the measured result to the controller 620.

\<Verify Integrated Target Structure (S812)\>

The controller 620 understands the characteristics of the charged particle beam transmitted in the step S810 and changes the structure of the integrated target structure 1 to be manufactured later in the step S806 depending on the understood result. That is, the controller 620 may finely change the structure of the integrated target structure 1 to be manufactured later to generate the desired charged particle beam.

In addition, the characteristics of the charged particle beam transmitted in the step S810 may be stored while being combined with the structure of the integrated target structure 1. Further, the stored result may be reflected to the simulation, etc., of the step S804.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An integrated target structure, comprising:
a target layer configured to emit charged particles depending on an irradiation of a laser beam;
an optical component configured to control at least one of the laser beam and the charged particles; and
a support body configured to support the target layer and the optical component using one structure,
wherein the optical component includes
a collimator configured to collimate the laser beam, and
wherein the optical components further includes at least one of:
a first filter configured to control characteristics of the laser beam;
an amplifier configured to amplify the laser beam; and
a second filter configured to pass charged particles having a specific energy among the charged particles emitted by the target layer.

2. The integrated target structure of claim 1, wherein the optical component includes the first filter, the amplifier, and the second filter, and
wherein the collimator, the first filter, and the amplifier are disposed between a source of the laser beam and the target layer, and the target layer is disposed between the collimator and the second filter.

3. The integrated target structure of claim 2, wherein the second filter is configured to pass charged particles having a first predetermined energy level, and to block charged particles having a second predetermined energy level, the first predetermined energy level being different than the second predetermined energy level.

4. The integrated target structure of claim 1, wherein the optical component includes the amplifier, the amplifier being hemispherical.

5. A medical appliance, comprising:
an integrated target structure;
a light source configured to irradiate a laser beam to the integrated target structure; and
a 3D printer configured to manufacture the integrated target structure,
wherein the integrated target structure includes:
a target layer configured to emit charged particles depending on an irradiation of the laser beam;
an optical component configured to control at least one of the laser beam and the charged particles; and
a support body configured to support the target layer and the optical component using one structure,
wherein the optical component includes:
a collimator configured to collimate the laser beam, and
wherein the optical component further includes at least one of:
a first filter configured to control characteristics of the laser beam;
an amplifier configured to amplify the laser beam; and
a second filter configured to pass charged particles having a specific energy among the charged particles emitted by the target layer.

6. The medical appliance of claim 5, further comprising:
a scanner configured to scan the integrated target structure manufactured by the 3D printer; and
a sensor configured to measure characteristics of the charged particles emitted by the integrated target structure.

7. The medical appliance of claim 5, wherein the optical component includes the first filter, the amplifier, and the second filter, and
wherein the collimator, the first filter, and the amplifier are disposed between the light source of the laser beam and the target layer, and the target layer is disposed between the collimator and the second filter.

8. The medical appliance of claim 7, wherein the second filter is configured to pass charged particles having a first predetermined energy level, and to block charged particles having a second predetermined energy level, the first predetermined energy level being different than the second predetermined energy level.

9. The medical appliance of claim 5, wherein the optical component includes the amplifier, the amplifier being hemispherical.

10. A driving method of a medical appliance, comprising:
tracking a position of a patient's tumor;
measuring characteristics of a laser beam generated from a light source;
simulating an integrated target structure for generating charged particles depending on the position of the tumor and the characteristics of the laser beam; and
manufacturing the integrated target structure using a 3D printer based on the simulated result.

11. The driving method of claim 10, further comprising:
scanning the integrated target structure manufactured by the 3D printer using a scanner; and
controlling the 3D printer depending on the scanned result.

12. The driving method of claim 10, further comprising:
irradiating the charged particles emitted from the integrated target structure to the tumor; and
measuring characteristics of the charged particles emitted from the integrated target structure.

13. The driving method of claim 10, wherein the integrated target structure includes:
a target layer configured to emit the charged particles depending on an irradiation of the laser beam;
an optical component configured to control at least one of the laser beam and the charged particles; and a support body configured to support the target layer and the optical component using one structure, wherein the optical component includes at least one of:
a collimator configured to collimate the laser beam;
a first filter configured to control characteristics of the laser beam;
an amplifier configured to amplify the laser beam; and
a second filter configured to pass charged particles having a specific energy among the charged particles emitted by the target layer.

14. The driving method of claim 13, wherein the optical component includes the collimator, the first filter, the amplifier, and the second filter, and
wherein the collimator, the first filter, and the amplifier are disposed between the light source of the laser beam and the target layer, and the target layer is disposed between the collimator and the second filter.

15. The driving method of claim 14, wherein the second filter is configured to pass charged particles having a first predetermined energy level, and to block charged particles having a second predetermined energy level, the first predetermined energy level being different than the second predetermined energy level.

16. The driving method of claim 13, wherein optical component includes the amplifier, the amplifier being hemispherical.

* * * * *